United States Patent [19]
Antrim et al.

[11] Patent Number: 5,756,714
[45] Date of Patent: May 26, 1998

[54] METHOD FOR LIQUEFYING STARCH

[75] Inventors: Richard L. Antrim, Solon, Iowa; Colin Mitchinson, Half Moon Bay, Calif.; Leif P. Solheim, Clinton, Iowa

[73] Assignee: Genencor International, Inc., Rochester, N.Y.

[21] Appl. No.: 411,038

[22] Filed: Mar. 27, 1995

Related U.S. Application Data

[63] Continuation-in-part of Ser. No. 401,325, Mar. 9, 1995, abandoned.

[51] Int. Cl.$^6$ .............................. A23J 1/14; A23L 1/211
[52] U.S. Cl. .................... 536/102; 435/96; 435/99; 435/202; 435/203; 435/204; 435/205
[58] Field of Search ........................... 536/102; 435/96, 435/99, 202, 203, 204, 205

[56] References Cited

U.S. PATENT DOCUMENTS

| | | |
|---|---|---|
| 3,663,369 | 5/1972 | Morehouse et al. |
| 3,852,504 | 12/1974 | Mihara et al. ............... 426/373 |
| 4,111,750 | 9/1978 | Colilla et al. |
| 4,261,868 | 4/1981 | Hora et al. |
| 4,284,722 | 8/1981 | Tamuri et al. |
| 4,376,824 | 3/1983 | Hurst et al. |
| 4,493,893 | 1/1985 | Mielenz et al. |
| 4,620,936 | 11/1986 | Kielman et al. |
| 4,634,551 | 1/1987 | Burns et al. |
| 4,647,538 | 3/1987 | Zeikus et al. |
| 4,732,973 | 3/1988 | Barr et al. |
| 4,752,585 | 6/1988 | Koths et al. |
| 4,760,025 | 7/1988 | Estell et al. |
| 4,863,626 | 9/1989 | Coyne et al. |
| 4,914,029 | 4/1990 | Caransa et al. ............... 435/101 |
| 4,931,554 | 6/1990 | Bijl et al. ............... 536/124 |
| 4,933,279 | 6/1990 | Carroll et al. |
| 4,997,665 | 3/1991 | Grethlein ............... 426/542 |
| 5,118,623 | 6/1992 | Boguslawski et al. |
| 5,180,669 | 1/1993 | Antrim |
| 5,346,823 | 9/1994 | Estell et al. |

FOREIGN PATENT DOCUMENTS

| | | |
|---|---|---|
| 0946/92 | 7/1992 | Denmark |
| 1503/92 | 12/1992 | Denmark |
| 0 285 123 | 5/1988 | European Pat. Off. |
| 0380343 | 8/1990 | European Pat. Off. |
| 0 409 299 | 1/1991 | European Pat. Off. |
| 0 410 498 | 1/1991 | European Pat. Off. |
| 0 676 456 | 11/1992 | France |
| 91/00353 | 1/1991 | WIPO |
| 91/16423 | 10/1991 | WIPO |
| 94/02597 | 2/1994 | WIPO |

OTHER PUBLICATIONS

Alexander, R., "Corn Dry Milling: Processes, Products, and Application" *Corn: Chemistry and Technology*, pp. 351–376, eds. Watson et al. (1987).

Antrim et al., "A New *Bacillus licheniformis* Alpha-Amylase Capable of Low pH Liquefaction" *Starch* 43(9):355–360 (1990).

Aschengreen, et al., "Liquefaction, Saccharification and Isomerization of Starches from Sources Other than Maize" *Starch* 31(9):64–66 (1979).

Bealinkelly et al, "Studies on the thermostability of the alpha–amylase of bacillus–caldovelox" *Appl. Microbiol. and Biotech* 36(3):332–336 (Dec. 1991).

Brosnan, et al., "Investigation of the mechanism of irreversible thermoinactivation of bacillus–stearothermophilus alpha–amylase" *Eur. J. of Biochem.* 203(1–2)225–231 (Jan. 1992).

Declerck, et al., "*Use of Amber Suppressors to Investigate the Thermostability of Bacillus licheniformis* α–Amylase" *J. of Biol. Chem.* 265(26):15481–15488 (1990).

Estell, et al., "Engineering an enzyme by Site–directed Mutagenesis to Be Resistant to Chemical Oxidation" *J. of Biol. Chem.* 260(11)6518–6521 (Jun. 1985).

Gray, et al., "Structural Genes Encoding the Thermophilic α–Amylases of *Bacillus sterothermophilus* and *Bacillus lichenmiformis*" *J. of Bacteriology* 166(2):635–643 (May 1986).

Holm, et al., "Random mutagenesis used to probe the structure and function of *Bacillus stearothermophilus* alpha–amylase" *Protein Engineering* 3(3)181–191 (1990).

Jain, *Handbook of Enzyme Inhibitors* (1965–1977) pp. 51–52, 333, eds. J. Wiley & Sons.

Janecek, et al., "α–Amylases and approaches leading to their enhanced stability" *FEBS* 11085 304(1,1–3):1–3 (Jun. 1992).

Jorgenesen, "Cloning of a chromosomal α–amylase gene from *Bacillus stearothermophilus*" *FEMS Microbiology Letters* 77:271–276 (1991).

Joyet, et al., "Hyperthermostable variants of a highly thermostable alpha–amylase" *Biotechnology* 10:1579–1583 (Dec. 1992).

Lehrfeld, "HPLC Separation and Quantitation of Phytic Acid and Some Inositol Phosphates in Foods: Problems and Solutions" *J. Agric. Food Chem.* 42:2726–2731 (1994).

Manning, et al., "Thermostable α–Amyulase of *Bacillus stearothermophilus*" *J. of Biol. Chem.* 236(11):2952–2965 (Nov. 1961).

Matsui, et al., "A mutant α–amylase with enhanced activity specific for short substrates" *FEBS* 11596 310(3):216–218 (Oct. 1992).

(List continued on next page.)

*Primary Examiner*—Nathan M. Nutter
*Attorney, Agent, or Firm*—Debra J. Glaister

[57] ABSTRACT

According to the invention a method is provided for liquefying starch comprising the steps of treating the starch prior to or simultaneously with liquefying the starch to inactivate and/or remove the enzyme inhibiting composition present in the starch and form treated starch; adding α-amylase to the treated starch; and reacting the treated starch for a time and at a temperature effective to liquefy the treated starch. Effective means to treat the starch include the addition of a phytate degrading enzyme and heat treatment, optionally followed by filtration or centrifugation, of granular starch or a starch solution.

17 Claims, No Drawings

OTHER PUBLICATIONS

Matsui et al., "An increase in the transglycosylation activity of *Saccharomycopsis* α-amylase altered by site-directed mutagenesis" *Biochimica et Biophysica Acta* 1077:416–419 (1991).

Matsuura et al., "Structure and Possible Catalytic Residues of Taka–Amylase A" *J. Biochemistry* 95:697–702 (1984).

Nakajima, et al., "Nucleotide Sequence of the *Bacillus stearothermophilus* α-Amylase Gene" *J. Bacteriology* 163(1):401–406 (Jul. 1985).

Ogasahara, et al., "Studies on Thermophilic α-Amylase from *Bacillus stearothermophilus*" *J. Biochem.* 67(1):65–89 (1970).

Ottesen et al., "The Subtilisins" *Methods in Enzymology* 19:199–215.

Sogaard et al., "Site–directed Mutagenesis of Histidine 93, Aspartic Acid 180, Glutamic Acid 205, Histidine 290, and Aspartic Acid 291 at the Active Site and Tryphtophan 279 at the Raw Starch Binding site in Barley α-Amylase 1" *J. Biol. Chem.* 268(32) 22480–22484 (Oct. 1993).

Suzuki, et al., "Amino Acid Residues Stabilizing a *Bacillus* α-Amylase against Irreversible Thermoinactivation" *J. Biol. Chem.* 264(32):18933–18938 (Nov. 1989).

Svensson, et al., "Mutational analysis of glucosylase function" *J. Biotech.* 29:1–37 (1993).

Takagi, et al., "Bacterial and Mold Amylases" pp. 234–271, eds. Lee et al.

Takase et al., "Site–directed mutagenesis of active site residues in *Bacillus subtilis* a–amylase" *Biochimica et Biophysica Acta* 1120–281–288 (1992).

Tomazic et al., "Mechanisms of Irreversible Thermal Inactivation of *Bacillus* α–Amylases" *J. of Biol. Chem.* 262(7):3086–3091 (Mar. 1988).

Udaka et al., "Bacterial Amylase Genes and Their Expression" *J.Jpn. Soc. Starch Sci.* 33(9):112–118 (1986).

Vihinen et al. "Site–Directed Mutagenesis of a Thermostable α-Amylase from *Bacillus stearothermophilus*: Punitive Role of Three Conserved Residues" *J. Biochem* 107:267–272 (1990).

Watson, "Manufacture of Corn and Milo Starches" pp. 31–51.

Yuuki et al., "Complete Nucleotide Sequence of a Gene Coding for Heat for Heat–and pH–Stable α–Amylase of *Bacillus licheniformis*: Comparison of the Amino Acid Sequence of three Bacterial Liquefying α–Amylases Deduced from the DNA Sequences" *J. Biochem* 98:1147–1156 (1985).

B.E. Knuckles et al. (1987) J. Food Science 52(3):719–721.

V. Hagenimana et al. (1994) J. Food Science 59(2):373–377.

J. Jaskari et al. (1995) Cereal Chem. 72(6):625–631.

E. Moore et al. (1995) J. Ind. Microbiol. 14:396–402.

METHOD FOR LIQUEFYING STARCH

CROSS-REFERENCE TO RELATED APPLICATIONS

This application is a continuation-in-part of U.S. application Ser. No. 08/401,325 filed Mar. 9, 1995, now abandoned and which is incorporated herein by reference in its entirety.

BACKGROUND OF THE INVENTION

The present invention relates to modifying the use of α-amylase in conversion of grain starch to downstream products, such as dextrose, fructose and alcohol. In particular, the present invention relates to the removal, and/or inactivation of an enzyme inhibiting composition from a granular starch prior to or during liquefaction.

Grains such as corn have long been used as a source of starch. One of the well known methods of separating and purifying starch for use in industrial processes is the wet-milling process. This method has developed into a highly specific and integrated system designed to separate the major components of a grain kernel as completely as possible (see Stanley A. Watson, *Starch: Chemistry & Technology*, Vol. II, *Industrial Aspects*, Academic Press, New York, 1967, pp. 30–51).

In a common wet-milling process, dry grains used for the production of starch products are first subjected to a soaking process called steeping. During steeping, the grains are subjected to a counterflow water current which separates many solubles, including phytate and phytic acid, sugars, salts and proteins, from the grain granules. The steeped grains are separated from the soaking water (steepwater) and subjected to mechanical cracking and grinding procedures. Flotation and centrifugation techniques are then used to separate germ from the starch, fiber and protein. The resulting slurry of endosperm (starch), fiber and protein is then further ground and screened to separate out the fiber. Finally, the protein and endosperm related components are separated based on density through countercurrent rinsing and centrifugation to separate the starch from the protein/gluten stream. The isolated starch stream is then extensively rinsed to remove any non-granular starch related solubles, including solubles such as inorganic salts, and compounds such as phytate and salts of phytic acid. The resulting product is a highly purified slurry of insoluble granular starch which serves as the starting product for conversion to fructose.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by α-amylase (EC 3.2.1.1.).

A common enzymatic liquefaction process involves adjusting the pH of a granular starch slurry to between 6.0 and 6.5, the pH optimum of α-amylase derived from *Bacillus licheniformis*, with the addition of calcium hydroxide, sodium hydroxide or sodium carbonate. The addition of calcium hydroxide has the advantage of also providing calcium ions which are known to stabilize the α-amylase against inactivation. Upon addition of α-amylase, the suspension is pumped through a steam jet to instantaneously raise the temperature to between 80°–115° C. The starch is immediately gelatinized and, due to the presence of α-amylase, depolymerized through random hydrolysis of a (1–4) glycosidic bonds by α-amylase to a fluid mass which is easily pumped.

In a second variation to the liquefaction process, α-amylase is added to the starch suspension, the suspension is held at a temperature of 80°–100° C. to partially hydrolyze the starch granules, and the partially hydrolyzed starch suspension is pumped through a jet at temperatures in excess of about 105° C. to thoroughly gelatinize any remaining granular structure. After cooling the gelatinized starch, a second addition of α-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using α-amylase. The general practice in the art is to undertake enzymatic liquefaction at a lower temperature when using the dry milling process. Generally, low temperature liquefaction is believed to be less efficient than high temperature liquefaction in converting starch to soluble dextrins.

Typically, after gelatinization the starch solution is held at an elevated temperature in the presence of α-amylase until a DE of 10–20 is achieved, usually a period of 1–3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

The maximum temperature at which the starch solution containing α-amylase can be held depends upon the microbial source from which the enzyme was attained and the molecular structure of the α-amylase molecule. α-amylases produced by wild-type strains of *B. subtilis* or *B. amyloliquefaciens* are typically used at temperatures no greater than about 90° C. due to excessively rapid thermal inactivation above that temperature, whereas α-amylases produced by wild-type strains of *B. licheniformis* can be used at temperatures up to about 110° C.

The presence of starch and calcium ion are known to stabilize α-amylases against inactivation. Nonetheless, α-amylases are used at pH values above 6 to protect against rapid inactivation. At low temperatures, α-amylase from *B. licheniformis* is known to display excellent hydrolyzing activity on starch substrate at pH values as low as 5. However, when the enzyme is used for starch hydrolysis at common jet temperatures, e.g., between 102° C. and 109° C., the pH must be maintained at least above pH 5.7 to avoid excessively rapid inactivation. The pH requirement unfortunately provides a narrow window of processing opportunity because pH values above 6.0 result in undesirable by-products, e.g., maltulose. Therefore, in reality, liquefaction pH must be maintained between 5.9 and 6.0 to attain a satisfactory yield of hydrolyzed starch.

Another problem relating to pH of liquefaction is the need to raise the pH of the starch suspension from about 4, the pH of a corn starch suspension as it comes from the wet milling stage, to 5.9–6.0. This pH adjustment requires the costly addition of acid neutralizing chemicals and also requires additional ion-exchange refining of the final starch conversion product to remove the chemical. Moreover, the next process step after liquefaction, typically saccharification of the liquefied starch into glucose, requires a pH of 4–4.5; therefore, the pH must be adjusted down from 5.9–6.0 to 4–4.5; requiring additional chemical addition and refining steps.

As is common in many plant seeds, phytic acid, the hexaphosphate ester of myoinositol, is known to be present in the grain kernels in the form of phytate salts, such as potassium, calcium and magnesium phytate. As indicated above, it has been the general belief that all significant quantities of phytic acid present in the corn kernels leach from the kernels during the steeping process to be removed from the liquefaction stream prior to further processing. Surprisingly, as herein described, Applicants have discovered that a form of phytate appears to be present in granular starch subsequent to steeping and extensive rinsing. While not wishing to be bound by theory, Applicants believe that residual phytate is actually bound within the starch granule itself and thus is not separated from the starch during the extensive rinsing processes.

In U.S. Pat. No. 5,322,778, liquefaction between pH 4.0 and 6.0 was achieved by adding an antioxidant such as bisulfite or a salt thereof, ascorbic acid or a salt thereof, erythorbic acid, or phenolic antioxidants such as butylated hydroxyanisole, butylated hydroxytoluene, or α-tocopherol to the liquefaction slurry. According to this patent, sodium bisulfite must be added in a concentration of greater than 5 mM.

In U.S. Pat. No. 5,180,669, liquefaction between a pH of 5.0 to 6.0 was achieved by the addition of carbonate ion in excess of the amount needed to buffer the solution to the ground starch slurry. Due to an increased pH effect which occurs with addition of carbonate ion, the slurry is generally neutralized by adding a source of hydrogen ion, for example, an inorganic acid such as hydrochloric acid or sulfuric acid.

In PCT Publication No. WO 94/02597, a mutant α-amylase having improved oxidative stability is described wherein one or more methionines are replaced by any amino acid except cysteine or methionine.

In PCT publication No. 94/18314, a mutant-amylase having improved oxidative stability is described wherein one or more of the methionine, tryptophan, cysteine, histidine or tyrosine residues is replaced with a non-oxidizable amino acid.

In PCT Publication No. WO 91/00353, the problems associated with liquefaction are approached by genetically engineering α-amylase to include characteristics including increased thermal, acid and alkaline stability.

In U.S. Pat. No. 4,914,029, phytase is added to the corn steep liquor to reduce the quantity of phytic acid in the corn steep liquor, and thus more efficiently utilize the corn steep liquor in animal feed.

Despite the advances made in the prior art, a need exists for an efficient means for starch liquefaction at low pH levels using commercially available α-amylase. Similarly, a need exists in the art for a method which allows liquefaction of dry milled grain at higher temperatures. Nonetheless, none of the methods described above provides the important advantages of allowing removal and/or inactivation of a composition responsible for inefficient or nonexistent enzyme assisted low pH starch liquefaction. Further, none of the methods described above allows a flexible approach to liquefaction which does not require the addition of antioxidants or a neutralizing acid, the preparation of a genetically engineered enzyme, or the discovery of a new α-amylase which has exceptional low pH stability characteristics.

SUMMARY OF THE INVENTION

It is an object of this invention to provide efficient low pH liquefaction of starch using readily available mutant or wild-type α-amylase enzymes.

It is a further object of this invention to provide for the removal and/or inactivation of an enzyme inhibiting composition present in granular starch which is primarily responsible for inefficient liquefaction by α-amylase at low pH.

It is a further object of this invention to provide a method of liquefying starch without the addition of costly antioxidants.

It is a further object of this invention to provide a simple and efficient manner of liquefying starch which permits flexibility in the method and does not require the use of genetically engineered α-amylase.

According to the invention a method is provided for liquefying starch comprising the steps of treating the starch prior to or simultaneously with liquefying the starch to inactivate and/or remove an enzyme inhibiting composition present in the starch and form treated starch; adding α-amylase to the treated starch; and reacting the treated starch for a time and at a temperature effective to liquefy the treated starch. According to another embodiment of the invention, a composition of matter is provided comprising a mixture of α-amylase and aqueous starch at a pH of less than 5.7, said composition containing either inactivated enzyme inhibiting composition or being substantially free of enzyme inhibiting inactivating composition.

As pointed out in greater detail below, practice of the present invention confers important advantages to commercial starch liquefaction processes. While not wishing to be bound by theory, Applicants believe that their discovery that a specific composition present in granular starch, not heretofore identified as a constituent thereof, is responsible for problems associated with low pH liquefaction of starch with α-amylase. From an elemental analysis of the isolated composition, this composition appears to comprise a form of phytate. The surprising identification of the composition responsible for low pH liquefaction problems allows the possibility of inactivating and/or removing the responsible agent and thus efficiently liquefying granular starch at low pH values, and as low as pH 4.5, with well known and characterized α-amylases. As shown below, Applicants' invention allows, for the first time, an approach to starch liquefaction at low pH which can be utilized with commercially viable systems including α-amylase. Moreover, the present invention does not require the use of specially designed mutant or wild type enzymes showing exceptional low pH stability characteristics, or costly measures such as addition of antioxidants or acid neutralization.

The invention itself, together with further objects and attendant advantages, will best be understood by reference to the following detailed description.

DETAILED DESCRIPTION OF THE INVENTION

"Liquefaction" or "liquefy" means a process by which starch is converted to shorter chain and less viscous dextrins. Generally, this process involves gelatinization of starch simultaneously with or followed by the addition of α-amylase.

"Steep liquor" means a liquid which is drawn from steeped grain kernels during the steeping process. The steep liquor contains a significant portion of the soluble components of the grain.

"Granular starch" or "starch granules" means a water-insoluble component of edible grains which remains after removal of the hull, fiber, protein, germ, and solubles through the steeping, mechanical cracking, separations, screening, countercurrent rinsing and centrifugation steps typical of the grain wet-milling process. Granular starch comprises intact starch granules containing almost exclusively packed starch molecules (i.e., amylopectin and amylose). In corn, the granular starch component comprises about 99% starch; the remaining 1% being comprised of protein, ash, fiber and trace components tightly associated with the granules. The packing structure of granular starch severely retards the ability of α-amylase to hydrolyze starch. Gelatinization of the starch is utilized to disrupt the granules to form a soluble starch solution and facilitate enzymatic hydrolysis.

"Starch solution" means the water soluble gelatinized starch which results from heating granular starch. Upon heating of the granules to above about 72° C., granular starch dissociates to form an aqueous mixture of loose starch molecules. This mixture comprising, for example, about 75% amylopectin and 25% amylose in yellow dent corn forms a viscous solution in water. In commercial processes to form glucose or fructose, it is the starch solution which is liquefied to form a soluble dextrin solution.

"Enzyme inhibiting composition" or "EIC" means a composition in granular starch which acts to inhibit α-amylase hydrolysis of a starch solution during low pH liquefaction. Chemical analysis of a composition (EIC) extracted from gelatinized starch granules which acts to inhibit α-amylase at low pH has revealed that EIC comprises a form of phytate. Forms of phytate which comprise the enzyme inhibiting composition are believed to be magnesium, iron, potassium, manganese, zinc and/or calcium salts of phytate.

"Treatment" is defined to mean the treatment of granular starch or a starch solution to decrease or eliminate an effect caused by the enzyme inhibiting composition during enzymatic hydrolysis of starch at low pH, e.g., below pH 5.7. Treatment includes, for example, addition of a compound or compounds to granular starch or a starch solution which acts to prevent the enzyme inhibiting composition from destabilizing, inactivating or otherwise lessening the starch hydrolyzing activity characteristic of α-amylase; subjecting granular starch or a starch solution to conditions or separation techniques to remove or significantly diminish the inhibiting property of the enzyme inhibiting composition prior to low pH liquefaction; or addition of a compound or compounds which removes the enzyme inhibiting composition from the solution through chemical modification of EIC to a non-EIC compound.

"α-amylase" means an enzymatic activity which cleaves or hydrolyzes the α(1-4) glycosidic bond, e.g., that in starch, amylopectin or amylose polymers. Suitable α-amylases are the naturally occurring α-amylases as well as recombinant or mutant amylases which are useful in liquefaction of starch. Preferred amylases in the present invention are α-amylases derived from Bacillus, and particularly *Bacillus licheniformis*, *Bacillus amyloliquefaciens* or *Bacillus stearothermophilus*.

Treatment of the starch according to the present invention, allows the liquefaction reaction, i.e., enzymatic hydrolysis of the starch, amylopectin or amylose, to be carried out efficiently at a pH of less than 6.0, or even less than 5.0, in contrast to prior art liquefaction methods. Preferably the liquefaction reaction is carried at a pH of between about 4.5 and about 5.7, more preferably between about 4.5 and about 5.5 and most preferably between about 4.5 and about 5.2.

In a preferred embodiment of the invention, granular starch or a starch solution is treated to inactivate an enzyme inhibiting composition present therein by heat treatment prior to the addition of α-amylase. In this embodiment, α-amylase is preferably added to the granular starch or starch solution subsequent to heating to ensure inactivation of the enzyme inhibiting composition without it first affecting the α-amylase. However, addition of α-amylase simultaneously with the treatment step is considered within the scope of the present invention. The slurry is then incubated for an appropriate time at an appropriate pH and at an appropriate temperature, as is well known in the art, to liquefy the starch. According to the present invention, the enzyme inhibiting composition can be significantly diminished in its ability to inhibit α-amylase activity by heating the starch solution prior to liquefaction, i.e., prior to the addition of α-amylase.

Alternatively, it is considered within the scope of the invention to first incubate the starch solution with amylase at a lower temperature, e.g., 60° C. to 90° C., to release the enzyme inhibiting composition from the starch or gelatinized starch solution prior to completing liquefaction. Subsequently, the temperature is raised to liquefy the starch by raising the temperature to an appropriate temperature and for an appropriate time sufficient to substantially liquefy the starch. Preferably, the temperature is raised to between about 80° C. to about 115° C. The inactivation of the enzyme inactivating composition may occur during the lower temperature incubation, or during the increase and holding of the temperature during liquefaction. In this embodiment, additional α-amylase may be added during the low temperature α-amylase incubation or during or after the subsequent liquefaction. As with the other embodiments of the invention, this embodiment will allow efficient liquefaction at pH values below 5.7.

In another preferred embodiment, the granular starch or starch solution is treated with a composition which chemically modifies or degrades the enzyme inhibiting composition so as to eliminate the enzyme inhibiting characteristic thereof and thus remove the enzyme inhibiting composition from the starch. Preferably, a phytate degrading enzyme is added to the starch granules or starch solution prior to liquefaction. A preferred phytate degrading enzyme comprises phytase or acid phosphatase. Many of the enzymes produced by microorganisms which catalyze the conversion of phytate to inositol and inorganic phosphate are broadly known as phytases. Phytase producing microorganisms comprise bacteria and filamentous fungi and yeasts, including *Bacillus subtilis*, Pseudomonas, *Saccharomyces cerevisiae*, *Aspergillus niger*, *Aspergillus nigervar. awamori*, *Aspergillus terreus*, *Aspergillus ficuum*. Preferably, the phytase is derived from *Aspergillus ficuum*. Purification of such phytase enzymes from microbial sources is accomplished by techniques known in the art. For example, in Ullah, et al., *Preparative Biochemistry*, 18(4), pp. 443–458 (1988) purification of a phytase derived from *Aspergillus ficuum* is described, which description is herein incorporated by reference.

The concentration of phytate degrading enzyme added to the granular starch or the starch solution should be effective to significantly degrade the enzyme inhibiting composition in the solution. Of course, determination of a suitable phytate degrading enzyme concentration is dependent on pH, temperature, reaction time, specific enzymatic activity and, additionally, the type of grain from which the granular starch or starch solution is obtained. However, optimal conditions for phytate degrading enzyme activity are easily ascertainable by one of skill in the art. Preferably, the concentration of phytate degrading enzyme is from about 0.1 to about 100 units of phytase (phytase unit) per gram of starch. More preferably, the concentration of phytate degrading enzyme is from about 1 to about 25 units of phytase per gram of starch. One phytase unit (phytate degrading activity) is defined as the amount of enzyme that will liberate 1 μmole of inorganic phosphorus (P) from 0.042M Mg—K phytate per minute at 37° C. (Sigma Chemical Co., St. Louis, Mo.). It is contemplated that phytate degrading enzyme be added to either the granular starch or to the starch solution. It is believed that phytate degrading enzymes are effective for the purposes of the present invention regardless of whether the starch is in granular form or soluble in solution. In fact, Applicants have discovered that adding a phytate degrading enzyme to the granular starch, i.e., prior to gelatinization, is effective in treating the solution according to the present invention. Alternatively, the phytase can be added to the starch solution during or after gelatinization.

According to another preferred embodiment, the enzyme inhibiting composition is inactivated and/or removed from the granular starch or starch solution prior to liquefaction. Removal of the enzyme inhibiting composition can be by any art recognized chemical or mechanical separation method which is effective at removing compounds including phytic acid or phytate salts from solution. Suitable separation methods include chromatography, ion-exchange, microfiltration and centrifugation. An especially preferred process comprises removal by pH dependent phytate precipitation or heat treatment followed by filtration or centrifugation. Also preferably, removal of the enzyme inhibiting composition is achieved through high temperature centrifugation or high temperature filtration.

The pH of the granular starch or starch solution during treatment is any pH which allows removal or inactivation of the enzyme inhibiting composition. While the treatment step can be performed at any pH level, treatment is efficient at a pH of between about 4 and about 6 because the need to undesirably adjust the pH level of the granular starch stream from the wet-milling process is eliminated. Preferably, the pH is between about 4.5 and about 5.7; more preferably, the pH is between about 4.5 and about 5.5; and most preferably between about 4.5 and about 5.2. It should be noted that by maintaining the pH of the treatment step in these ranges, the pH of the treatment step will correlate well to that of the wet milled grain starch processing stream, thus avoiding excessive cost associated with adjusting the pH of the wet milled corn.

The temperature of the treatment step is a suitable temperature for removal or inactivation of the enzyme inhibiting composition, and may depend on the specific mode of treatment chosen. Where the treatment step comprises the addition of phytase, a temperature should be chosen which is suitable for hydrolysis activity for the specific enzyme. For microbial phytase, a suitable temperature will generally be between about 20° C. and about 60° C. and preferably between about 30° C. and about 40° C. However, the development of temperature resistant phytase enzymes which are capable of hydrolyzing phytate at temperatures of, for example, 100°–110° C. are specifically contemplated as being within the scope of the present invention and are preferred. Where the treatment step comprises heat treatment, optionally followed by filtration or centrifugation, the temperature should be greater than the gelatinization temperature of the starch; preferably between about 80° C. and about 150° C., more preferably between about 90° C. and about 110° C., and most preferably between about 95° C. and about 110° C.

The time for the treatment step may also vary with the specific type of treatment chosen. Where the treatment step comprises addition of phytase, the treatment time will be dependent on the specific activity of the phytase enzyme added and the temperature of the incubation. With microbial phytase, the treatment time is preferably from about 1 to about 24 hours and more preferably from about 3 to about 6 hours, depending on conditions. Where the treatment step comprises removal of the enzyme inhibiting composition from the granular starch or the starch solution by heat treatment, optionally followed by filtration or centrifugation, the treatment time is preferably from about 10 seconds to about 60 minutes, and more preferably from about 3 to about 10 minutes. It is believed that inactivation of the phytate from granular starch may be essentially instantaneous under appropriate conditions, such as heat, and thus, the treatment time may be limited only by technical restraints.

Following heat treatment, centrifugation or filtration may be used to separate the inactivated phytate from solution by art recognized means. Where centrifugation is used to separate the phytate from the starch during treatment, centrifugation may be carried out at a g force of at least 2000×g and preferably at a g force of between about 5000×g and about 10,000×g.

Treating conditions may also be affected by the type of grain or milling used. For example, a grain which contains a relatively high concentration of enzyme inhibiting composition may require a longer treatment than that of a grain which has a lower concentration of enzyme inhibiting composition. Varying levels of phytic acid content in different vegetable matter is disclosed in Lehrfield, J. Agric. Food Chem., Vol. 42, pp. 2726–2731 (1994), herein incorporated by reference. When the grain is prepared for liquefaction by the dry milling process, a much larger amount of phytate is likely to be present than in the wet milling process due to the presence of the fiber and protein fraction. Thus, treatment of dry milled starch may require more stringent conditions than wet milled starch.

Subsequent to, or simultaneously with, treating the granular starch or starch solution to inactivate and/or remove the enzyme inhibiting composition, α-amylase is added to the starch to liquefy the starch to lower molecular weight dextrins. Thus, it is contemplated as within the scope of the invention to either treat the granular starch or starch solution prior to or simultaneously with liquefaction using α-amylase. The liquefaction can be performed according to any well known liquefaction technique which utilizes α-amylase. The pH during the liquefaction step according to the invention is preferably less than about 5.7, more preferably less than 5.3, and most preferably between about 4.5 and about 5.

The following examples are representative, and not limitative, of the advantages conferred through the use of the invention. However, one of ordinary skill in the art would be able to substitute conditions, grains, temperature, enzymes and the like according to the above disclosure.

EXAMPLES

Example 1

Assay for α-Amylase Activity Determination

α-Amylase activity was determined through an assay which depends on the ability of starch to form a blue colored complex with iodine and the disappearance of this color when starch is hydrolyzed to shorter dextrin molecules. The α-amylase activity was defined in terms of the digestion time required to produce a color change denoting a definite state of dextrination of the starch.

Reagents used were as follows: Phosphate buffer—Potassium dihydrogen phosphate (340 g) and sodium hydroxide (25.3 g) were dissolved in water and diluted to ~2 liters. The buffer was cooled to room temperature and the pH was adjusted to 6.2±0.1. The buffer was diluted to 2 liters in a volumetric flask. Starch substrate—Ten grams (dry substance) of soluble lintner starch were suspended in 50 ml of water and washed into ~300 ml of boiling water. The suspension was again brought to boiling and was boiled for 5 minutes with constant stirring. The starch solution was cooled with constant stirring to room temperature and 125 ml of phosphate buffer was added. The solution was diluted to 500 ml with water. The starch substrate was made fresh daily. Stock iodine solution—Iodine crystals (5.5 g) and potassium iodide (11.0 g) were dissolved in water and were volumetrically diluted to 250 ml. The solution was kept from light. Dilute iodine solution—Potassium iodide (20 g) and 2 ml of stock iodine solution were dissolved in water and diluted volumetrically to 500 ml. The solution was made fresh daily. Enzyme diluting solution—Calcium chloride (11.1 g) was dissolved in 4 liters of water. Water used for all reagents was either distilled or deionized.

The unknown α-amylase sample was diluted to between 10–15 LU/ml (as defined below) with enzyme diluting solution. For many commercial α-amylase preparations a suitable dilution was found to be 2000 fold. Five milliliter aliquots of dilute iodine solution were dispensed into 13×100 mm test tubes and 10 ml of starch substrate was placed in a 23×200 mm test tube. All tubes were placed in the 30° C. water bath. A Hellige comparator equipped with a special α-amylase color disc (catalog number 620-s5) was used to make readings. Five milliliters of diluted enzyme (also at 30° C.) were mixed with the starch substrate and timing was begun. At appropriate time intervals, for Example 1 minute intervals early in the reaction and 15 second intervals later in the reaction, 1 ml aliquots of the enzyme-substrate mixture were transferred to a tube containing the attemperated dilute iodine solution. The starch iodine solution was mixed and transferred to a 13 mm precision square tube and the color was compared with the standard α-amylase color disc in the Hellige comparator. When the time of the end point was approached, samples were taken at 0.25 minute intervals.

The time required for the colors of the samples and the color disc to match were recorded and the activity (in liquefons per gram or ml) was calculated according to the formula:

$$LU/ml \text{ or } LU/g = \frac{570}{V \times t} \times D$$

Where
LU=liquefon unit
V=volume of enzyme (5 ml)
t=dextrinization time (minutes)
D=dilution factor: dilution volume the ÷ milliliters or grams of enzyme diluted.

Example 2

Starch Liquefaction Conditions—

Determination of Liquefied Starch DE (Dextrose Equivalent)

Starch liquefaction was performed using a reactor composed of 50 feet of 0.24 inch diameter (0.21 inch i.d.) stainless steel tubing bent into an approximately 10 inch diameter coil~5.5 inches high. The coil was equipped with an 11.5 inch in-line static mixer (Cole-Parmer #G-04669-60) mounted ~4 feet from the anterior end. The posterior end of the coil was equipped with a Swagelok in-line adjustable pressure relief value (# SS-4CA-3) set at a cracking pressure of about 20 psi. Starch slurry was fed to the coil at a rate of ~70 ml/minute with a piston metering pump. The coil was heated by immersion in a glycerol-water bath heated to 105.5° C. Temperature in the bath was maintained using a circulating heater\temperature controller (Fisher Scientific model 7305).

Granular starch was obtained from a corn wet miller and used within two days. As another source of starch, LO-DEX™ 10 (a water-soluble purified dextrin produced by the limited hydrolysis of corn starch), was purchased from American Maize-Products Company, Hammond, Ind. The LO-DEX™ 10 used herein had an initial DE of ~9.5.

The starch or maltodextrin was diluted to a desired solids level of about 30–35% dry solids with deionized water and the pH was adjusted with 2.5% NaOH or 6% HCl as required. Calcium was added in the form of $CaCl_2 \cdot 2H_2O$. Typical liquefaction conditions were:

| | |
|---|---|
| Starch or LO-DEX ™ 10 | 30%–35% solids |
| Calcium | 40–60 ppm (30 ppm added) |
| pH | 5.0–6.0 |
| α-Amylase | 12–14 LU/g of carbohydrate (dry basis) |

Starch or LO-DEX™ 10 containing enzyme and calcium in the form of $CaCl_2 \cdot 2H_2O$ was introduced into the reactor at about 70 ml/min. The temperature of the reactor was held at 105.5° C. by immersion of the reactor in a glycerol-water bath. Samples of starch were transferred from the reactor to a 95° C. second stage liquefaction bath and held for 90 minutes. The degree of starch liquefaction was measured immediately after the second stage liquefaction by determining the dextrose equivalent (DE) of the sample according to the method described in the *Standard Analytical Methods of the Member Companies of the Corn Refiners Association, Inc.*, sixth ed., Analytical Procedure Committee (1980).

Example 3

HPLC Analysis of Phytate

Analysis for phytate was accomplished through HPLC (high performance liquid chromatography) as follows. An HPLC system consisting of a Millipore/Waters, model 510 Waters Automated Gradient Controller, a 250 mm by 4.6 mm (i.d.) column packed with Poros 20 PI/M resin (PerSeptive Biosystems) and a Dionex conductivity detector equipped with a Dionex anion suppressor and a Dionex SRS controller was used. Samples of commercial phytate, EIC derived from corn gluten stream, ground whole corn, steep, ground whole wheat flour, ground rice, and EIC from the granular starch were diluted with deionized water to between 10–200 mg/L phytate and filtered to remove any insoluble material. Between 20 and 500 ml of the sample (depending upon phytate concentration) were injected into the column and the column was washed with water for 2 minutes at a flow rate of 1.3 ml/min. After 2 minutes, a linear gradient from 0 to 40 mM NaOH was begun and proceeded over the next 20 minutes at a flow rate of 1.3 ml/min.

Phytate eluted from the column after ~15 minutes. A linear series of dilutions of sodium phytate (Sigma Chemical Company, #P 8810) was used to calibrate the response of the conductivity detector. The EIC from each source was found to result in elution peaks identical to commercial phytate.

Example 4

Isolation of EIC from Corn Gluten Stream

A composition which inactivates or inhibits α-amylase was isolated from a protein rich starch stream (called the corn gluten stream) generated during corn endosperm fractionation in a corn wet milling plant as follows. Insoluble protein and starch granules were removed from the corn gluten fraction (~18.6% solids) by centrifugation (~6000×g for 15 min.). The supernatant was further clarified by vacuum filtration through Whatman #3 filter paper. The filtrate was fractionated by ultrafiltration using a 5,000 molecular weight cut off polysulfone hollow fiber cartridge (A/G Technology Corp., model UFP-5-D-4). Approximately 1200 ml of filtrate from the ultrafiltration step were adjusted to pH 9 by addition of 1N NaOH. The precipitate that formed was recovered by centrifugation (~6000×g for 10 minutes) and washed by resuspension in water.

After recovery of the precipitate from the wash water by centrifugation (~6000×g for 10 minutes), the precipitate was resuspended in ~500 ml of water and was dissolved by adjusting the pH slowly to 5 by the drop-wise addition of 3M HCl. The solution was filtered through Whatman #3 filter paper to remove any undissolved material and the filtrate was cooled to ~4° C. Two volumes of ethanol (at 4° C.) were added to the filtrate and the resulting precipitate was recovered by filtration through a fritted glass filter. The precipitate was washed with cold ethanol, recovered and placed in vacuum at room temperature to dry.

The 1200 ml of ultrafiltrate yielded 3.04 g of EIC.

Example 5

Inhibition of α-Amylase by EIC During Liquefaction at Low pH

EIC (from 0 to 200 mg/liter) isolated as in Example 4 was added to 35% LO-DEX™ 10 (pH 5.2) containing 50 ppm calcium. α-amylase (SPEZYME® AA20, produced by *B. licheniformis* and available commercially from Genencor International, Inc., South San Francisco, Calif.) was added at a rate of 12 LU/g carbohydrate and the pH of the solution was adjusted and maintained at pH 5.2 by the addition of 2.5% NaOH or 6% HCl as required. The solution was hydrolyzed using the reactor system described in Example 2. The degree of hydrolysis of the LO-DEX™ 10 was measured by dextrose equivalent (DE) immediately following the secondary hold.

Table 1 illustrates that increasing concentrations of EIC reduce the final DE of liquefied LO-DEX™ 10 (initial DE 9.5), indicating increased inhibition of the α-amylase.

TABLE 1

Effect of EIC on the α-Amylase Catalyzed Hydrolysis of LO-DEX™ 10 at pH 5.2

| EIC (mg/Liter) | DE |
| --- | --- |
| 0 | 18.7 |
| 50 | 17.5 |
| 100 | 15.8 |
| 150 | 13.9 |
| 200 | 12.9 |

As can be seen from this example, the presence of EIC significantly reduces the effectiveness of α-amylase at pH 5.2.

Example 6 pH Dependency of EIC Inhibition of α-Amylase

EIC (200 mg/liter) isolated as in Example 4 was added to 35% LO-DEX™ 10 containing 50 ppm calcium and the pH was adjusted to approximately 6.0 or 5.2. α-amylase (SPEZYME® AA20, produced by *B. licheniformis* and available commercially from Genencor International, Inc.) was added at a rate of 12 LU/g carbohydrate and the pH of the solution was adjusted and maintained at either pH 5.2 or 6.0 by the addition of 2.5% NaOH or 6% HCl as required. The solution was hydrolyzed using the reactor system and procedure described in Example 2. Identical controls but not containing EIC were performed at pH 5.2 and 6.0 at the same time as the test samples. The degree of hydrolysis of the LO-DEX™ 10 was measured by dextrose equivalent (DE) immediately following the secondary hold.

The results are tabulated in Table 2. As can be seen, the inhibition of α-amylase by EIC during hydrolysis of LO-DEX™ 10 is pH dependent. At pH 6.0 addition of 200 mg/L EIC caused only a ~6% reduction in DE development. At pH 5.2 DE development was reduced ~65%.

TABLE 2

Effect of pH upon EIC Inhibition of α-Amylase During Hydrolysis of LO-DEX™ 10

| pH | EIC (mg/L) | DE |
| --- | --- | --- |
| 6.0 | 0 | 19.2 |
| 6.0 | 200 | 18.6 |
| 5.2 | 0 | 18.7 |
| 5.2 | 200 | 12.9 |

Example 7

Elemental Analysis of EIC

EIC isolated from the corn gluten fraction as in Example 4 was subjected to elemental analysis by atomic adsorption spectroscopy (Galbraith Laboratories, Inc., Knoxville, Tenn.). The results are provided in Table 3.

TABLE 3

Elemental Analysis of EIC

| Carbon | 7.41% | Magnesium | 10.32 |
| --- | --- | --- | --- |
| Hydrogen | 2.48 | Manganese | 0.07 |
| Nitrogen | <0.05 | Zinc | 0.05 |
| Phosphorus | 22.38 | Iron | 0.04 |
| Calcium | 0.78 | Ash | 69.50 |

This analysis was consistent with that of a mixture of magnesium, manganese, zinc or iron salts of phytic acid. Subsequently, the EIC was analyzed for phytate content by HPLC analysis as described in Example 3. The analysis indicated that the anionic component of EIC was substantially comprised of phytate.

Example 8

Isolation of EIC from Ground Whole Corn 250 g of ground whole corn were suspended in 500 g of deionized water and the pH of the resulting slurry was adjusted to 4 with 6% HCl. The slurry was stirred for ~8 hours then allowed to stand for ~10 hours. The slurry was separated by filtration on Whatman #3 filter paper and the filtrate (~310 g) was adjusted to pH 9 with 1M NaOH. The generated precipitate was recovered by filtration through a 0.45 m membrane filter and washed with water. The precipitate was suspended in water to form a solution and the pH was adjusted to 5 by the slow addition of 6% HCl. The solution was filtered to remove any insoluble material and chilled to ~4° C. Two volumes of cold ethanol were added and the precipitate that formed was recovered by centrifugation. The precipitate was washed once with cold ethanol and dried over night under vacuum at room temperature.

From 250 g of ground whole corn, 0.772 g of EIC were recovered. EIC was confirmed by HPLC analysis for its characteristic phytate presence as in Example 3. Identification of EIC was confirmed by addition of the isolated EIC to a liquefaction mixture of LO-DEX™ 10 at pH 5.2 and determining whether α-amylase was inhibited. EIC (200 mg/liter) from ground whole corn was added to 35% LO-DEX™ 10 containing 50 ppm calcium ion in the form of $CaCl_2 \cdot 2H_2O$ and the pH was adjusted to approximately 5.2. α-amylase (SPEZYME® AA20, produced by *B. licheniformis* and available commercially from Genencor International, Inc.) was added at a rate of 12 LU/g carbohydrate and the pH of the solution was adjusted to pH 5.2 by the addition of 2.5% NaOH or 6% HCl as required. The solution was hydrolyzed using the reactor system and procedure described in Example 2. An identical control but containing no EIC was performed at pH 5.2 at the same time as the test sample. The degree of hydrolysis of the LO-DEX™ 10 was measured by dextrose equivalent (DE) immediately following the secondary hold.

The results of the trials, shown in the Table 4 below are consistent with those generated when using EIC isolated from the corn gluten stream shown above.

TABLE 4

Effect of EIC Isolated from Ground Whole Corn on
α-Amylase Stability During Hydrolysis of LO-DEX ™ 10 at pH 5.2

| Sample | DE |
| --- | --- |
| 200 mg/L EIC | 9.5 |
| Control | 16.3 |

HPLC analysis of EIC isolated from ground whole corn was performed as described in Example 3. One hundred microliters of a 15 mg/L solution of EIC was injected into the HPLC column and only one anionic peak, identified by elution time as phytate, was found in the material. The HPLC profile was substantially identical with that for EIC isolated from the corn gluten fraction.

Example 9

Isolation of EIC from Corn Steep Liquor

Heavy corn steep liquor obtained from a corn wet milling plant, i.e., an evaporated steepwater concentrate, having a density of ~19 Bé was clarified by centrifugation. One liter of clarified liquor was adjusted from pH 4.2 to 8.1 by the addition of 5M NaOH. The resultant precipitate was collected by centrifugation, was suspended in water to wash the precipitate and was again collected by centrifugation. The precipitate was suspended in ~400 ml of water and the pH of the slurry was adjusted to ~4 by the slow addition of 6% HCl. After the precipitate had dissolved the solution was filtered through Whatman #3 filter paper to remove any insoluble material and the filtrate was cooled to ~4° C. EIC was precipitated from solution by the addition of 2 volumes of ice cold ethanol and collected by centrifugation. The precipitate was washed once with cold ethanol, collected by centrifugation and vacuum dried at room temperature.

From 1 liter of heavy corn steep liquor, 23.3 g of EIC were recovered. Identification of EIC was confirmed by evaluation of α-amylase inactivation during hydrolysis of LO-DEX™ 10 at pH 5.2 and by HPLC analysis for phytate.

To determine the effect of EIC from corn steep liquor on liquefaction using α-amylase, 200 mg/liter was added to 35% LO-DEX™ 10 containing 50 ppm calcium ion in the form of $CaCl_2 \cdot 2H_2O$ and the pH was adjusted to approximately 5.2. α-amylase (SPEZYME® AA20, produced by *B. licheniformis* and available commercially from Genencor International, Inc.) was added at a rate of 12 LU/g carbohydrate and the pH of the solution was adjusted to pH 5.2 by the addition of 2.5% NaOH or 6% HCl as required. The solution was hydrolyzed using the reactor system and procedure described in Example 2. An identical control but containing no EIC was performed at pH 5.2 for comparison. The degree of hydrolysis of the LO-DEX™ 10 was measured by dextrose equivalent (DE) immediately following the secondary hold. An identical control was performed at pH 5.2 except for having no added EIC.

Results are shown in Table 5. These results are consistent with those generated when using EIC isolated from the corn gluten stream shown above.

TABLE 5

Effect of EIC Isolated from Corn Steep Liquor on
α-Amylase Stability During Hydrolysis of LO-DEX ™ 10 at pH 5.2

| Sample | DE |
| --- | --- |
| 200 mg/L EIC | 10.9 |
| Control | 14.9 |

HPLC analysis of EIC isolated from corn steep liquor was performed as described in Example 3. One hundred microliters of a 200 mg/L solution of EIC was injected into the HPLC column and only one anionic peak, identified by elution time as phytate, was found in the material. The HPLC profile was substantially identical with that for EIC isolated from the corn gluten fraction.

Example 10

Identification of EIC in Granular Corn Starch

A granular corn starch slurry from a corn wet miller was filtered over Whatman #3 filter paper to separate the water from the starch granules. The granular starch was resuspended in deionized water and refiltered to remove any water soluble components from the insoluble starch. The granular starch was then resuspended in water and diluted to 35% solids. α-amylase (12 LU/g carbohydrate) from *B. licheniformis* (SPEZYME® AA20, commercially available from Genencor International, Inc.) and calcium (50 ppm) were added and the granular starch slurry was liquefied at pH 5.2 as described in Example 2.

The water recovered from the first filtration of the corn starch slurry was used to dissolve LO-DEX™ 10 to produce a 35% solids solution. α-amylase (12 LU/g carbohydrate) and calcium ion added as $CaCl_2 \cdot 2H_2O$ (50 ppm) was added and the solution was liquefied at pH 5.2 as described in Example 2. A control containing LO-DEX™ 10 dissolved in deionized water, rather than the filtrate water from corn starch slurry was liquefied at the same time.

EIC was not detected in the filtrate water from the granular starch slurry when analyzed for its characteristic phytate presence by HPLC. HPLC analysis of pH 6 liquefied granular corn starch, however, detected an elution peak which indicated the presence of an identical substance to the EIC isolated from corn gluten in Example 4. HPLC analysis showed the presence of between 30 and 40 mg of phytate per liter of 30% solids by weight liquefied granular starch. Comparing liquefaction results of α-amylase in maltodextrin mixed with granular starch filtrate water and α-amylase in LO-DEX™ 10 mixed with deionized water confirmed that the EIC present in granular starch was not removed by washing. Accordingly, the results of these experiments, shown in Table 6 below, suggest that EIC responsible for α-amylase inactivation during starch liquefaction is associated with the starch granules, not free in solution.

TABLE 6

Liquefaction With Filtrate Water From Washed Corn Starch Granules

| Sample | 90 min. DE |
|---|---|
| Washed Starch Granules | ~0 |
| LO-DEX ™ 10 in Deionized Water | 17.9 |
| LO-DEX ™ 10 in Filtrate Water from Starch Slurry | 18.1 |

Example 11

Phytase Inactivation of EIC 20 ml of EIC isolated as in Example 4 was treated with 500 units of phytase (from *A. ficuum*, Sigma Chemical Company, P 9792) for 30 minutes at pH 2.5, 37° C. 10 ml of the treated EIC was added to LO-DEX™ 10 to yield 1 liter of 35% LO-DEX™ 10 solution containing 50 ppm calcium ion added as $CaCl_2 \cdot 2H_2O$ and 200 mg/l EIC. α-amylase derived from *B. licheniformis* (SPEZYME® AA20, commercially available from Genencor International, Inc.) was added at a rate of 12 LU/g carbohydrate and the solution was liquefied at pH 5.2 using the reactor system and process described in Example 2, above. Controls consisting of LO-DEX™ 10 with no added EIC and LO-DEX™ 10 containing 200 mg/ml untreated EIC were liquefied at the same time. As shown in Table 7, phytase treatment inactivates EIC thus preventing its ability to inhibit α-amylase.

TABLE 7

Phytase Treatment on EIC Inactivation of α-Amylase

| Sample | 90 min. DE |
|---|---|
| EIC-Free Control | 15.4 |
| 200 mg/L EIC | 9.5 |
| 200 mg/L Phytase-Treated EIC | 14.4 |

Example 12

Phytase Treatment of Granular Corn Starch

Phytase (from *A. ficuum*, 5 ml of 250 units/ml obtained from Sigma Chemical Co., St. Louis, Mo., product no. P9792) was added to 1 liter of 34% granular corn starch containing ~50 ppm calcium ion added as $CaCl_2 \cdot 2H_2O$ and were incubated for 5 hours at 37° C., pH 4.0. After incubation the pH of the granular starch slurry was adjusted to pH 5.2 and 12 LU/g of carbohydrate α-amylase derived from *B. licheniformis* (SPEZYME® AA20, commercially available from Genencor International, Inc.) was added to the granular starch slurry. The mixture was liquefied using the reactor system described in Example 2. A pH 5.2 control liquefaction using 34% granular corn starch slurry that had not been treated with phytase was performed at the same time.

In a second trial, phytase (from wheat, Sigma Chemical Company P1259, 160 units) was incubated with 1 liter of 35% granular corn starch slurry containing ~50 ppm calcium ion added as $CaCl_2 \cdot 2H_2O$ for 6 hours at 55° C., pH 5.15. After incubation, the pH of the granular starch slurry was adjusted to pH 5.5 and 12 LU/g carbohydrate of α-amylase derived from *B. licheniformis* (SPEZYME® AA20, commercially available from Genencor International, Inc.) was added to the slurry. The mixture was liquefied using the reactor system and process as described in Example 2. A pH 5.5 control liquefaction using 35% granular corn starch slurry not treated with phytase was performed at the same time.

As shown in Table 8, phytase treatment of granular corn starch prior to liquefaction increases the ability of α-amylase to hydrolyze starch at low pH.

TABLE 8

Effect of Phytase on α-Amylase Stability During Low pH Liquefaction

| | 90 min. DE | |
|---|---|---|
| Liquefaction pH | Control | Phytase Treated Starch |
| 5.2 | ~0 | 1.4 |
| 5.5 | 6.4 | 8.6 |

Example 13

Heat Filtration of Maltodextrin Containing EIC

EIC (200 mg/liter) isolated as in Example 4 was added to 35% w/w LO-DEX™ 10 containing 50 ppm calcium added in the form of $CaCl_2 \cdot 2H_2O$ and the pH was adjusted to approximately 5.2. The solution was divided into two parts. One part was heated to ~100° C. and immediately vacuum filtered through Whatman #3 filter paper while hot. The second part was vacuum filtered through Whatman #3 filter paper while at room temperature (e.g., 20°–25° C.). α-amylase (SPEZYME® AA20, produced by *B. licheniformis* and available commercially from Genencor International, Inc.) was added to each solution at a rate of 12 LU/g carbohydrate and the pH of each solution was adjusted to pH 5.2 by the addition of 2.5% NaOH or 6% HCl as required. Each solution was hydrolyzed using the reactor system and procedure described in Example 2. The degree of hydrolysis of the LO-DEX™ 10 was measured by dextrose equivalent (DE) immediately following the secondary hold. Samples of both solutions taken before hydrolysis were analyzed for phytate as described in Example 3.

As shown in Table 9, filtration of EIC-containing LO-DEX™ 10 at ~100° C. removes approximately 75% of the EIC from solution. As a result, less α-amylase was inactivated during liquefaction at pH 5.2 and the DE of the resultant hydrolysate was substantially greater.

TABLE 9

Effect of Hot Filtration on EIC Inactivation of α-Amylase During Low pH Liquefaction

| Sample | EIC Conc. | DE |
|---|---|---|
| Cold Filtered Maltodextrin | 184 mg/L | 11.5 |
| Hot Filtered Maltodextrin | 45 mg/L | 14.5 |
| "Unhydrolyzed" Maltodextrin | — | 9.5 |

Example 14

Isolation of EIC from Brown Rice

Brown Basmati rice (available commercially from Lundburg Mills) was ground to flour consistency using a small coffee grinder. Two hundred grams of the ground rice was added to 500 ml of deionized water and the pH was adjusted to ~3 with 6% Hcl. The slurry was allowed to stand for 30 hours with occasional stirring and then fractionated by vacuum filtration through Whatman #3 filter paper.

The pH of the filtrate was adjusted to 9 by addition of 1M NaOH and the precipitate that developed was recovered by centrifugation. The precipitate was washed once with water, recollected by centrifugation and resuspended in water. The pH of the suspension was slowly adjusted to ~5 by the dropwise addition of 6% HCl and the suspension was stirred to dissolve the precipitate. Undissolved material was removed by filtration through a 5 m membrane filter and the filtrate was chilled to ~4° C. Two volumes of cold ethanol were added to the filtrate and the precipitate that formed was recovered by centrifugation. The precipitate was washed once with cold ethanol and dried under vacuum at room temperature.

Two hundred grams of ground rice yielded 0.3571 g of EIC. The identification of EIC was confirmed by evaluation of α-amylase inactivation during hydrolysis of LO-DEX™ 10 at pH 5.2 and by HPLC analysis for phytate.

EIC (200 mg/liter) from ground rice was added to 35% LO-DEX™ 10 containing 50 ppm calcium ion added as $CaCl_2 \cdot 2H_2O$ and the pH was adjusted to approximately 5.2. α-amylase derived from *B. licheniformis* (SPEZYME AA20, commercially available from Genencor International, Inc.) was added at a rate of 12 LU/g carbohydrate and the pH of the solution was adjusted to pH 5.2 by the addition of 2.5% NaOH or 6% HCl as required. The solution was hydrolyzed using the reactor system and procedure as described in Example 2. An identical control but containing no EIC was performed at pH 5.2 at the same time as the test sample. The degree of hydrolysis of the LO-DEX™ 10 was measured by dextrose equivalent (DE) immediately following the secondary hold. The results of the trials are shown in Table 10.

TABLE 10

Effect of EIC Isolated from Ground Rice on α-Amylase Stability During Hydrolysis of LO-DEX ™ 10 at pH 5.2

| Sample | DE |
| --- | --- |
| Control | 16.3 |
| 200 mg/L EIC | 11.7 |

HPLC analysis of EIC isolated from ground rice was performed as described in Example 3. One hundred microliters of a 15 mg/L solution of EIC was injected into the HPLC column and only one anionic peak, identified by elution time as phytate, was found in the sample. The HPLC profile was substantially identical with that for EIC isolated from the corn gluten fraction.

Example 15

Isolation of EIC from Whole Wheat Flour

Two hundred grams of commercial whole wheat flour (commercially available from Arrowhead Mills) was added to 500 ml of deionized water containing 12 mM D,L-dithiothreitol (Sigma Chemical Co.). The pH of the slurry was adjusted to ~3 with 6% HCl and the slurry was allowed to stand at room temperature for ~30 hours with occasional stirring. The slurry was fractionated by centrifugation.

The pH of the filtrate was adjusted to 9 by addition of 1M NaOH and the precipitate that developed was recovered by centrifugation. The precipitate was washed once with water, recollected by centrifugation and resuspended in water. The pH of the suspension was slowly adjusted to ~5 by the dropwise addition of 6% HCl and the suspension was stirred to dissolve the precipitate. Undissolved material was removed by filtration through a 5 m membrane filter and the filtrate was chilled to ~4° C. Two volumes of cold ethanol were added to the filtrate and the precipitate that formed was recovered by centrifugation. The precipitate was washed once with cold ethanol and dried under vacuum at room temperature.

Two hundred grams of whole wheat flour yielded 0.385 g of EIC. The identification of EIC was confirmed by evaluation of α-amylase inactivation during hydrolysis of LO-DEX™ 10 at pH 5.2 and by HPLC analysis for phytate.

EIC (150 mg/liter) from whole wheat flour was added to 35% LO-DEX™ 10 containing 50 ppm calcium and the pH was adjusted to approximately 5.2. α-amylase derived from *B. licheniformis* (SPEZYME® AA20, available commercially from Genencor International, Inc.) was added at a rate of 12 LU/g carbohydrate and the pH of the solution was adjusted to pH 5.2 by the addition of 2.5% NaOH or 6% HCl as required. The solution was hydrolyzed using the reactor system and procedure as described in Example 2.

A control containing no EIC was performed under the same conditions for comparison. The degree of hydrolysis of the LO-DEX™ 10 was measured by dextrose equivalent (DE) immediately following the secondary hold. The results of the trials are shown in Table 11.

TABLE 11

Effect of EIC Isolated from Whole Wheat Flour on α-Amylase Stability During Hydrolysis of LO-DEX ™ 10 at pH 5.2

| Sample | DE |
| --- | --- |
| Control | 16.3 |
| 150 mg/L EIC | 14.2 |

HPLC analysis of EIC isolated from whole wheat flour was performed as described in Example 3. One hundred microliters of a 15 mg/L solution of EIC was injected into the HPLC column and only one anionic peak, identified by elution time as phytate, was found in the sample. The HPLC profile was substantially identical with that for EIC isolated from the corn gluten fraction.

Example 16

Precipitation of EIC by Heating to 95° C.

EIC (200 mg/L) isolated as in Example 4 was added to 35% w/w LO-DEX™ 10 containing 50 ppm calcium ion (added as $CaCl_2 \cdot 2H_2O$) and the pH was adjusted to 5.2 with 2.5% NaOH. The LO-DEX™ 10 solution was divided into two parts. One part was heated to 95° C. for ~6 minutes by passing the solution through the reactor described in Example 2. After passing through the reactor, α-amylase (SPEZYME® AA20, produced by *B. licheniformis* and available commercially from Genencor International, Inc.) was added to the solution at a rate of 12 LU/g of carbohydrate. The solution was then incubated at 95° C. for 90 minutes. The degree of hydrolysis of the LO-DEX™ 10 was measured by dextrose equivalent (DE) immediately following the 90 minute incubation.

The second part of the EIC-containing maltodextrin solution was dosed with α-amylase (12 LU/g carbohydrate, SPEZYME® AA20, produced by *B. licheniformis* and available commercially from Genencor International, Inc.) and put through the reactor system as described in Example 2, except that the temperature was 95° C. The solution was then incubated at 95° C. for 90 minutes. The degree of hydrolysis of the LO-DEX™ 10 was measured by dextrose equivalent (DE) immediately following the 90 minute incubation. An identical control but containing no EIC was run at the same time at pH 5.2 for comparison.

The results of the trials, shown in Table 12, show that the ability of EIC to inactivate α-amylase during liquefaction can be reduced by heating.

TABLE 12

Effect of Heating on EIC Inactivation of α-Amylase

| Sample | DE |
|---|---|
| Control | 17.6 |
| EIC + α-Amylase | 14.0 |
| EIC + α-Amylase added after Heating | 17.5 |

Example 17

Precipitation of EIC from Maltodextrin by Heating to 105.5° C.

EIC (200 mg/L) isolated as in Example 4 was added to 35% w/w LO-DEX™ 10 containing 50 ppm calcium ion (added as $CaCl_2 \cdot 2H_2O$) and the pH was adjusted to 5.2 with 2.5% NaOH. The LO-DEX™ 10 solution was divided into two parts. One part was heated to 105.5° C. for ~6 minutes by passing the solution through the reactor described in Example 2. After passing through the reactor, α-amylase (SPEZYME® AA20, produced by *B. licheniformis* and available commercially from Genencor International, Inc.) was added to the solution at a rate of 12 LU/g of carbohydrate. The solution was then incubated at 95° C. for 90 minutes. The degree of hydrolysis of the LO-DEX™ 10 was measured by dextrose equivalent (DE) immediately following the 90 minute incubation.

The second part of the EIC-containing maltodextrin solution was dosed with α-amylase (12 LU/g carbohydrate, SPEZYME® AA20, produced by *B. licheniformis* and available commercially from Genencor International, Inc.) and put through the reactor system as described in Example 2, at a temperature of 105.5° C. The solution was then incubated at 95° C. for 90 minutes. The degree of hydrolysis of the LO-DEX™ 10 was measured by dextrose equivalent (DE) immediately following the 90 minute incubation. An identical control but containing no EIC was run simultaneously at pH 5.2 for comparison.

The results of the trials, shown in Table 13, illustrate that the ability of EIC to inactivate α-amylase during liquefaction can be reduced by heating prior to the addition of α-amylase.

TABLE 13

Effect of Heating on EIC Inactivation of α-Amylase During Low pH Liquefaction

| Sample | DE |
|---|---|
| No EIC Control | 15.0 |
| EIC + α-Amylase | 10.2 |
| EIC + α-Amylase after Heating | 17.5 |

The presence of EIC in the LO-DEX™ is believed responsible for the increase in DE observed after adding EIC and heat treatment when compared to the control without any added EIC and no heat treatment.

Of course, it should be understood that a wide range of changes and modifications can be made to the preferred embodiment described above. It is therefore intended that the foregoing detailed description be understood that it is the following claims, including all equivalents, which are intended to define the scope of this invention.

We claim:

1. A method for liquefying starch comprising the steps of:
   (a) treating said starch prior to or simultaneously with liquefying said starch to inactivate and/or remove an enzyme inhibiting composition present in said starch to form treated starch;
   (b) adding α-amylase to said starch; and
   (c) liquefying said treated starch.

2. The method according to claim 1, wherein said step (a) comprises adding an enzyme comprising phytate degrading activity to said starch.

3. The method according to claim 2, wherein said enzyme comprising phytate degrading activity is added simultaneously with said α-amylase.

4. The method according to claim 2, wherein said enzyme comprising phytate degrading activity is added at a concentration between about 0.1 and about 100 phytase units per gram starch.

5. The method according to claim 1, wherein said step (a) comprises heating said starch to a temperature of between about 80° C. and about 150° C. prior to the addition of α-amylase to inactivate said enzyme inhibiting composition.

6. The method according to claim 5, further comprising removing said enzyme inhibiting composition by centrifugation.

7. The method according to claim 6, wherein said centrifugation is carried out subsequent to or simultaneously with raising the temperature of said starch.

8. The method according to claim 1, wherein said step (b) is carried out simultaneously with said step (a).

9. The method according to claim 1, wherein said step (b) is carried out subsequent to said step (a).

10. The method according to claim 1, wherein said step (c) is carried out at a pH of less than 6.0.

11. The method according to claim 1, wherein said step (c) is carried out at a pH of between about 4.5 and about 5.7.

12. The method according to claim 1, wherein said step (c) is carried out at a pH of between about 4.5 and about 5.2.

13. The method according to claim 9, wherein prior to said step (a), α-amylase is added to said starch at a temperature of between about 60° C. and about 90° C. to release said enzyme inhibiting composition from said starch.

14. The method according to claim 13, wherein said step (a) comprises heat treatment subsequent to adding said α-amylase to release said enzyme inhibiting composition from said starch by heating said starch for a time and at a temperature sufficient to inactivate said enzyme inhibiting composition.

15. A method for inactivating a hydrolyzing enzyme comprising adding an enzyme inhibiting composition to an aqueous mixture including said hydrolyzing enzyme.

16. The method according to claim 15, wherein said hydrolyzing enzyme comprises α-amylase.

17. The method according to claim 14 wherein said enzyme inhibiting composition comprises phytate or a salt thereof.

* * * * *